(12) United States Patent
Zerfas et al.

(10) Patent No.: US 7,458,971 B2
(45) Date of Patent: Dec. 2, 2008

(54) RF ABLATION PROBE WITH UNIBODY ELECTRODE ELEMENT

(75) Inventors: Jeff W. Zerfas, Bloomington, IN (US); Steve Pickett, Spencer, IN (US); James A. Teague, Spencer, IN (US); Martin G. Donfrio, Gosport, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 405 days.

(21) Appl. No.: 10/949,081

(22) Filed: Sep. 24, 2004

(65) Prior Publication Data
US 2006/0074412 A1    Apr. 6, 2006

(51) Int. Cl.
*A61B 18/14* (2006.01)
(52) U.S. Cl. .................................................... 606/41
(58) Field of Classification Search .................... 606/41
See application file for complete search history.

(56) References Cited

U.S. PATENT DOCUMENTS

| | | | |
|---|---|---|---|
| 5,551,426 A | | 9/1996 | Hummel et al. |
| 5,855,576 A | | 1/1999 | LeVeen et al. |
| 6,142,993 A | * | 11/2000 | Whayne et al. .............. 606/41 |
| 6,221,071 B1 | * | 4/2001 | Sherry et al. .................. 606/41 |
| 2004/0116920 A1 | | 6/2004 | Rioux et al. |
| 2005/0065509 A1 | * | 3/2005 | Coldwell et al. .............. 606/41 |
| 2005/0107781 A1 | * | 5/2005 | Ostrovsky et al. ............. 606/41 |

FOREIGN PATENT DOCUMENTS

| | | |
|---|---|---|
| WO | WO 02/22032 A1 | 9/2001 |
| WO | WO 2005/048862 A2 | 11/2004 |

OTHER PUBLICATIONS

PCT International Search Report for PCT/US2005/030299, Applicant:—Boston Scientific Scimed, Inc., Forms PCT/ISA/210 and 220, dated Jan. 10, 2006 (7 pages).
PCT Written Opinion of the International Search Authority for PCT/US2005/030299, Applicant:—Boston Scientific Scimed, Inc., Form PCT/ISA/237, dated Jan. 10, 2006 (6 pages).

* cited by examiner

*Primary Examiner*—Lee S Cohen
(74) *Attorney, Agent, or Firm*—Vista IP Law Group LLP

(57) ABSTRACT

An ablation probe and method of manufacturing the ablation probe are provided. The probe comprises a probe shaft and a unibody electrode element. The unibody electrode element comprises a common electrode base located at the distal end of the shaft, and a plurality of electrode tines distally extending from the electrode base. The electrode element may be created by forming divisions (such as slits or slots) from a first end of an electrically conductive elongate member towards an opposing second end of the elongate member. Alternatively, the divisions can be formed from a first end of an electrically conductive sheet towards an opposing second end of the sheet, and then bent or rolled to form the elongate member. In either case, the common electrode base can either be separately mounted to a probe shaft, or the probe shaft can be formed from the elongate member, in which case, the electrode base will be integrated with the probe shaft as a unibody structure. The electrode tines can be optionally shaped, e.g., to proximally evert.

33 Claims, 6 Drawing Sheets

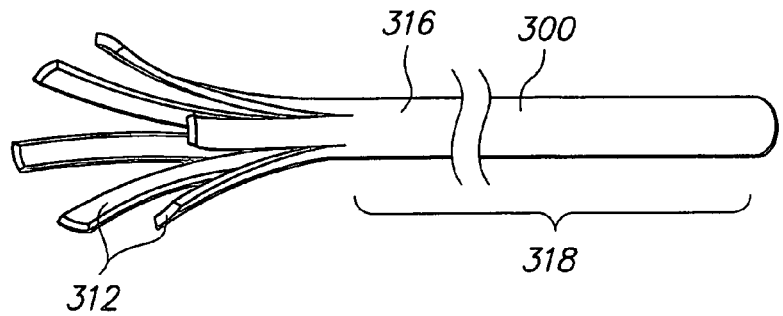
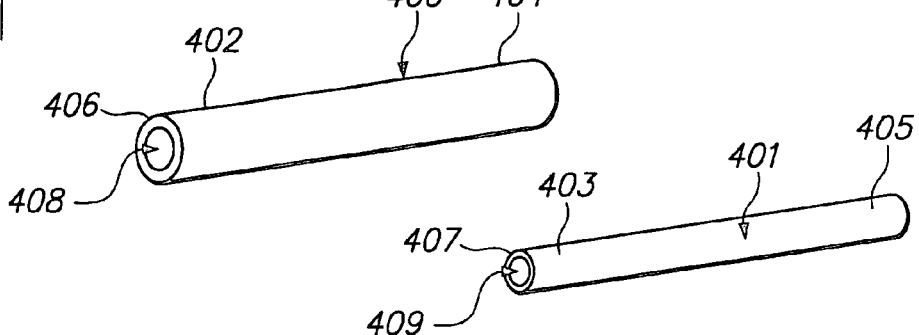
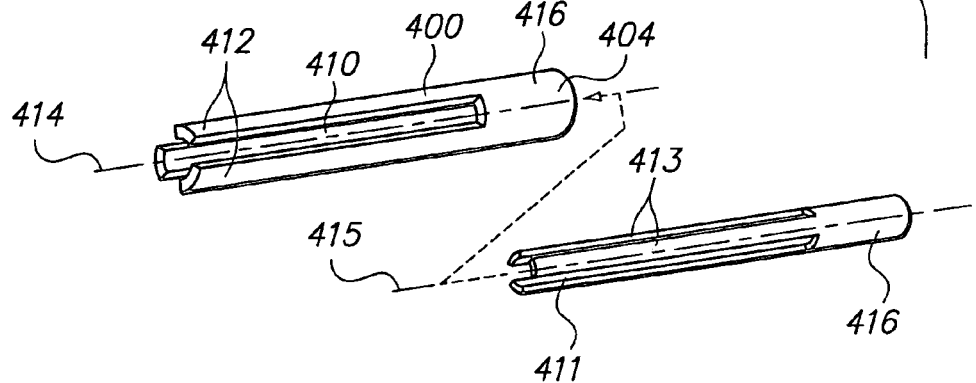
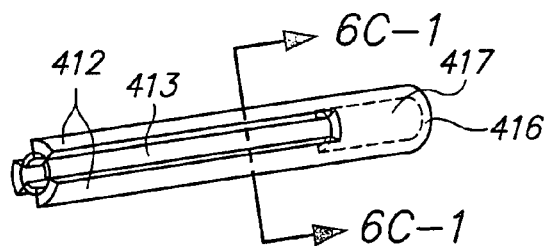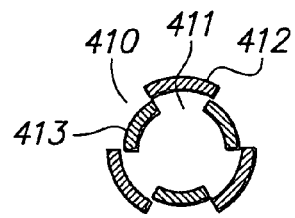

RF ABLATION PROBE WITH UNIBODY ELECTRODE ELEMENT

FIELD OF THE INVENTION

The field of the invention relates generally to the structure and use of radio frequency (RF) electrosurgical probes for the treatment of tissue, and more particularly, to electrosurgical probes having multiple tissue-penetrating electrodes that are deployed in an array to treat large volumes of tissue.

BACKGROUND OF THE INVENTION

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction. In particular, radio frequency ablation (RFA) may be used to treat patients with tissue anomalies, such as liver anomalies and many primary cancers, such as cancers of the stomach, bowel, pancreas, kidney and lung. RFA treatment involves destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of electrode tines deployable from a cannula. Each of the tines includes a proximal end that is coupled to a generator, and a distal end that may project from a distal end of the cannula. The tines are arranged in an array with the distal ends located generally radially and uniformly spaced apart from the distal end of the cannula. The tines may be energized in a bipolar mode (i.e., current flows between closely spaced electrode tines) or a monopolar mode (i.e., current flows between one or more electrode tines and a larger, remotely located common electrode) to heat and necrose tissue within a precisely defined volumetric region of target tissue. To assure that the target tissue is adequately treated and/or to limit damaging adjacent healthy tissues, the array of tines may be arranged uniformly, e.g., substantially evenly and symmetrically spaced-apart so that heat is generated uniformly within the desired target tissue volume.

When using the above described devices in percutaneous interventions, the cannula is generally inserted through a patient's skin, and the tines are deployed out of the distal end of the cannula to penetrate target tissue. The tines are then energized to ablate the target tissue. Such procedure results in surgical wounds that are much smaller in size than those associated with open surgical settings, and therefore, improves healing time for the patient. However, the size of a surgical wound is still affected by the overall cross sectional dimension of the ablation device—i.e., the larger the ablation device used, the larger the wound size.

The above described devices are generally constructed by manufacturing the tines in individual pieces, and welding or soldering the tines onto a shaft. Such manufacturing technique is time consuming, and increases the risk of manufacturing error. Also, the connection adhering the individual tines to the shaft increases the overall cross sectional dimension of the ablation device, which in turn, increases the size of surgical wounds when the ablation device is used to treat patients.

Thus, there remains a need to provide for improved methods of manufacturing ablation devices.

SUMMARY OF THE INVENTION

In accordance with a first aspect of the present inventions, a tissue ablation probe is provided. The probe comprises a probe shaft, which may be cylindrical, and a unibody electrode element. The unibody electrode element comprises a common electrode base located at the distal end of the shaft, and a plurality of electrode tines distally extending from the electrode base. The electrode tines may either be tightly spaced or loosely spaced at the electrode base, and may be pre-shaped, e.g., in a proximally everted shape. In one embodiment, the electrode element and shaft are formed as a unibody structure. In another embodiment, the electrode element and shaft are formed as discrete members that are subsequently secured to each other.

The electrode element may be electrically coupled to the probe shaft. In an optional embodiment, the probe comprises a radio frequency connector secured to the proximal end of the shaft end and electrically coupled to the electrode tines, either through the probe shaft or another means, such as RF wires. The probe may optionally comprise a cannula, in which case, the probe shaft is slidably disposed therein, so that the electrode element can be alternately placed in a deployed configuration and a retracted configuration. The probe may optionally comprise another unibody electrode element comprising another common electrode base coaxially secured to the electrode base and another plurality of electrode tines distally extending from the other electrode base.

In accordance with a second aspect of the present inventions, another tissue ablation probe is provided. The probe comprises a probe shaft, which may be cylindrical, a common electrode base located at the distal end of the probe shaft, and an array of electrode tines distally extending from the electrode base. The electrode array has a cross-sectional profile at the electrode base that is equal to or less than the cross-sectional profile of the electrode base, itself. The detailed features of the probe shaft, electrode base, and electrode tines can be the same as those previously described above.

In accordance with a third aspect of the present inventions, a method of manufacturing an ablation probe is provided. The method comprises forming divisions from a first end of an electrically conductive elongate member towards an opposing second end of the elongate member to create a plurality of electrode tines and a common electrode base from the elongate member. Alternatively, the divisions can be formed from a first end of an electrically conductive sheet towards an opposing second end of the sheet, and then bent or rolled to form the elongate member. In either case, the common electrode base can either be separately mounted to a probe shaft, or the probe shaft can be formed from the elongate member, in which case, the electrode base will be integrated with the probe shaft as a unibody structure. In one embodiment, the elongate member is a hollow cylinder, although other shapes can be used. The divisions can be variously formed in the elongate member to create the electrode tines. For example, the divisions can take the form of slits, such that the electrode tines are tightly spaced at the electrode base. Or the divisions can be slots, such that the electrode tines are loosely spaced at the electrode base. The electrode tines can be optionally shaped, e.g., to proximally evert.

The method may optionally comprise electrically coupling the electrode tines to the probe shaft. A radio frequency connector can also be mounted to the probe shaft and electrically coupled to the electrode tines via the probe shaft or another means, such as RF wires. The method may also comprise mounting the probe shaft within a cannula, so that the electrode tines can be alternately placed in a deployed configuration and a retracted configuration. In one method, divisions are formed from a first end of another electrically conductive elongate member towards an opposing second end of the other elongate member to create another plurality of electrode tines and another common electrode base from the other elongate member. In this case, the other electrode base can be coaxially secured within the first electrode base in order to integrate the assembly.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 5A-5D are perspective views illustrating another method of constructing the ablation probe of FIGS. 2 and 3;

FIGS. 6A-6E are perspective views illustrating still another method of constructing the ablation probe of FIGS. 2 and 3;

DETAILED DESCRIPTION OF THE EMBODIMENTS

Figure 1:
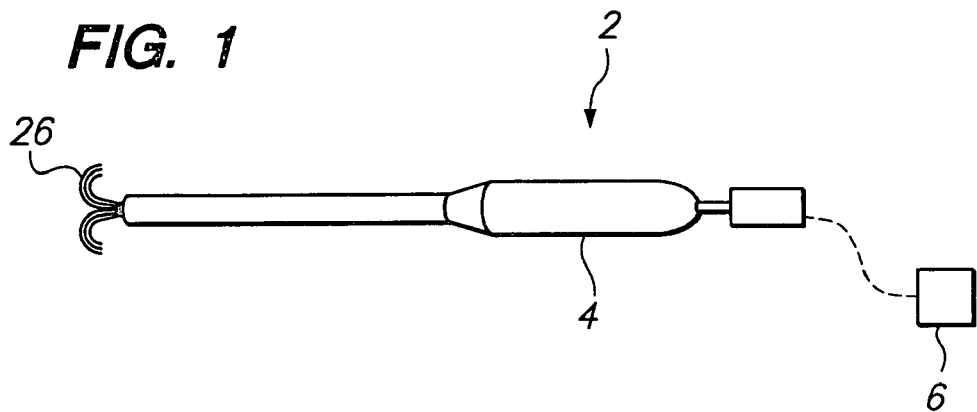
FIG. 1 is a schematic diagram of a tissue ablation system constructed in accordance with the present invention.

FIG. 1 illustrates a tissue ablation system 2 constructed in accordance with one embodiment of the invention. The tissue ablation system 2 generally includes a probe assembly 4 configured for introduction into the body of a patient for ablative treatment of target tissue, and a radio frequency (RF) generator 6 configured for supplying RF energy to the probe assembly 4 in a controlled manner.

Figure 2:
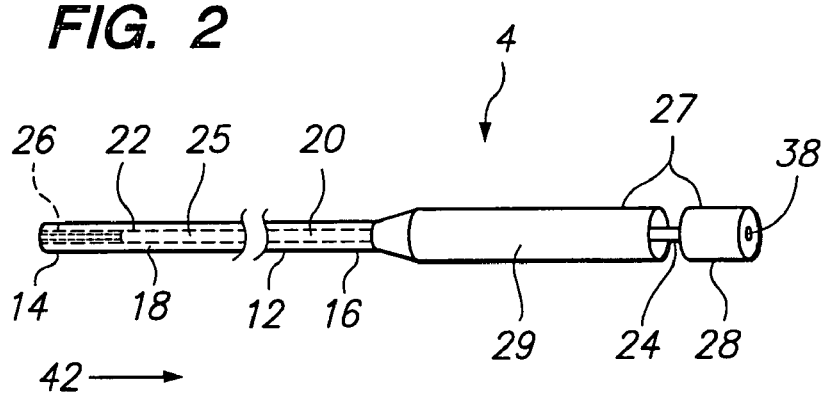
FIG. 2 is a perspective view of an ablation probe used in the system of FIG. 1, wherein an electrode array is particularly shown retracted.
Figure 3:
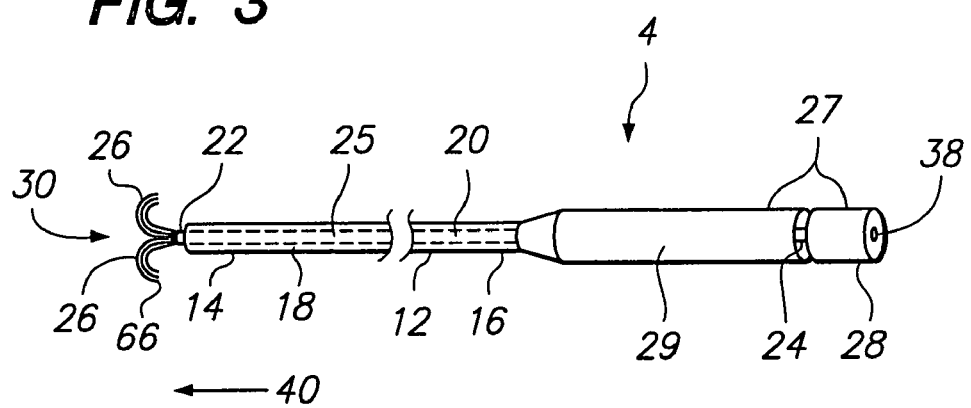
FIG. 3 is a perspective view of an ablation probe used in the system of FIG. 1, wherein an electrode array is particularly shown deployed.

Referring specifically now to FIGS. 2 and 3, the probe assembly 4 includes an elongate cannula 12, a shaft 20 slidably disposed within the cannula 12, and a plurality of electrodes 26 carried by the shaft 20. The cannula 12 has a distal end 14, a proximal end 16, and a central lumen 18 extending through the cannula 12 between the distal end 14 and the proximal end 16. The cannula 12 may be rigid, semi-rigid, or flexible depending upon the designed means for introducing the cannula 12 to the target tissue. The cannula 12 is composed of a suitable material, such as plastic, metal or the like, and has a suitable length, typically in the range from 5 cm to 30 cm, preferably from 10 cm to 20 cm. The length of the cannula 12 can also have other dimensions. If composed of an electrically conductive material, the cannula 12 is preferably covered with an insulative material. The cannula 12 has an outside cross sectional dimension consistent with its intended use, typically being from 0.5 mm to 5 mm, usually from 1.3 mm to 4 mm. The cannula 12 may have an inner cross sectional dimension in the range from 0.3 mm to 4 mm, preferably from 1 mm to 3.5 mm. The cannula 12 may also have other outside and inner cross sectional dimensions.

It can be appreciated that longitudinal translation of the shaft 20 relative to the cannula 12 in a distal direction 40 deploys the electrode tines 26 from the distal end 14 of the cannula 12 (FIG. 3), and longitudinal translation of the shaft 20 relative to the cannula 12 in a proximal direction 42 retracts the shaft 20 and the electrode tines 26 into the distal end 14 of the cannula 12 (FIG. 2). The shaft 20 comprises a distal end 22 and a proximal end 24. Like the cannula 12, the shaft 20 is composed of a suitable material, such as plastic, metal or the like. As will be described in further detail below, the material from which the shaft 20 is constructed will ultimately depend on the material from which the electrodes 26 are composed and the manner in which the electrodes 26 are secured to the shaft 20.

In the illustrated embodiment, each electrode 26 takes the form of an electrode tine, which resembles the shape of a needle or wire. Each of the electrodes 26 is in the form of a small diameter metal element, which can penetrate into tissue as it is advanced from a target site within the target region. In some embodiments, distal ends 66 of the electrodes 26 may be honed or sharpened to facilitate their ability to penetrate tissue. The distal ends 66 of these electrodes 26 may be hardened using conventional heat treatment or other metallurgical processes. They may be partially covered with insulation, although they will be at least partially free from insulation over their distal portions.

When deployed from the cannula 12, the array 30 of electrodes 26 is placed in a three-dimensional configuration that usually defines a generally ellipsoidal or spherical volume having a periphery with a maximum radius in the range from 0.5 to 4 cm. The electrodes 26 are resilient and pre-shaped to assume a desired configuration when advanced into tissue. In the illustrated embodiment, the electrodes 26 diverge radially outwardly from the cannula 12 in a uniform pattern, i.e., with the spacing between adjacent electrodes 26 diverging in a substantially uniform and/or symmetric pattern. In the illustrated embodiment, the electrodes 26 also evert proximally, so that they face partially or fully in the proximal direction when fully deployed.

In exemplary embodiments, pairs of adjacent electrodes 26 can be spaced from each other in similar or identical, repeated patterns and can be symmetrically positioned about an axis of the shaft 20. It will be appreciated that a wide variety of particular patterns can be provided to uniformly cover the region to be treated. It should be noted that although a total of six electrodes 26 are illustrated in FIG. 3, in other embodiments, the probe assembly 4 can have more or fewer than six electrodes 26. It should be noted that the shape and configuration of the electrodes 26 should not be limited to that described previously, and that the electrodes 26 may have other pre-formed shapes, such as a spiral shape or a dove-tail shape, and may be spaced from each other in a non-uniform pattern.

The electrodes 26 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrodes 26 may also be made from any of a wide variety of stainless steels. The electrodes 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the electrodes 26 to be visualized in-situ, and their alloys may be tailored to accomplish an appropriate blend of flexibility and stiffness. They may be coated onto the electrodes 26 or be mixed with another material used for construction of the electrodes 26.

The electrodes 26 have generally uniform widths and rectangular cross-sections. In this manner, the electrodes 26 can be easily formed from the distal end of the shaft 20, as will be described in further detail below. The rectangular cross-sections also make the electrodes 26 stiffer in one direction (e.g., the transverse direction) and more flexible in another direction (e.g., the radial direction). By increasing transverse stiffness, proper circumferential alignment of the electrodes 26 within the lumen 18 of the cannula 12 is enhanced. As will be described in further detail below, the widths of the electrodes 26 may be non-uniform, and the cross-sections of the electrodes 26 may be non-rectangular. Exemplary electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm.

In the illustrated embodiment, the RF current is delivered to the electrode array 30 in a monopolar fashion, which means that current will pass from the electrode array 30, which is configured to concentrate the energy flux in order to have an injurious effect on the surrounding tissue, and a dispersive electrode (not shown), which is located remotely from the electrode array 30 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank.

Alternatively, the RF current is delivered to the electrode array 30 in a bipolar fashion, which means that current will pass between two electrodes ("positive" and "negative" electrodes) of the electrode array 30, or between the electrodes of the electrode array 30 and the electrodes of another array ("positive" and "negative" electrode arrays). In a bipolar arrangement, the positive and negative electrodes or electrode arrays will be insulated from each other in any regions where they would or could be in contact with each other during the power delivery phase.

Returning to FIGS. 2 and 3, the probe assembly 4 further includes a handle assembly 27, which includes a member 28 mounted to the proximal end 24 of the shaft 20, and a handle sleeve 29 mounted to the proximal end 16 of the cannula 12. The handle member 28 is slidably engaged with the handle sleeve 29 (and the cannula 20). The handle member 28 also includes an electrical connector 38, which allows the probe assembly 2 to be connected to the generator 6 during use. The electrical connector 38 is electrically coupled to the electrodes 26. As will be described in further detail below, the electrical connector 38 can be conveniently coupled to the electrodes 26 via the shaft 20 (which will be electrically conductive), although in other embodiments, the connector 38 can be coupled to the electrodes 26 via separate wires (not shown). The handle member 28 and the handle sleeve 29 can be composed of any suitable rigid material, such as, e.g., metal, plastic, or the like.

Optionally, a marker (not shown) may be placed on the handle member 28 and/or on the proximal end 24 of the shaft 20 for indicating a rotational orientation or a position of the handle member 28 relative to the shaft 20 (and the electrodes 26) during use. In some embodiments, the handle assembly 27 can have an indexing feature. For example, the proximal end 24 of the shaft 20 or the handle member 28 can have one or more keys that mate with respective slot(s) at the interior surface of the cannula 12 or the handle sleeve 29. Such indexing feature allows circumferential alignment of the shaft 20 (and the array 30) relative to the cannula 12. Angle indexing devices that may be used include those described in U.S. patent application Ser. No. 10/317,796, entitled "Angle Indexer For Medical Devices", the entire disclosure of which is expressly incorporated by reference herein. In other embodiments, the handle member 28 may also include a locking mechanism (not shown) to temporarily lock against the shaft 20 to provide a more stable indexing. For example, the locking mechanism may include an axially-sliding clutch assembly that is slidable along an axis of the shaft 20 to thereby secure the handle member 28 against the shaft 20. Other securing devices known in the art may also be used.

Referring back to FIG. 1, the RF generator 6 is electrically connected to the electrical connector 38, which may be directly or indirectly (e.g., via a conductor) electrically coupled to the electrode array 30. The RF generator 6 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., which markets these power supplies under the trademarks RF2000 (100 W) and RF3000 (200 W).

Further details regarding electrode array-type probe arrangements are disclosed in U.S. Pat. No. 6,379,353, which is hereby expressly incorporated by reference.

Having generally described the system 2, various processes that can be used to manufacture and secure electrode arrays to a probe shaft, while reducing the number of welds or bonds and the cross-sectional space required to house the electrode arrays, will now be described.

Figure 4A:
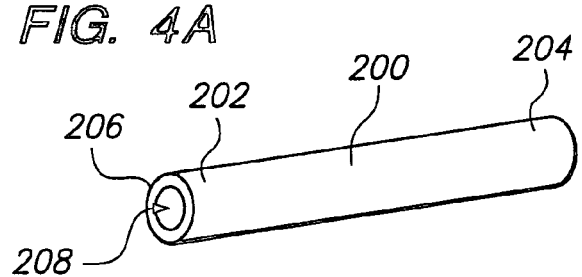
FIGS. 4A-4E are perspective views illustrating one method of constructing the ablation probe of FIGS. 2 and 3.

FIGS. 4A-4E illustrate one process for manufacturing and securing a unibody electrode array onto a shaft. First, an elongate member 200 is provided (FIG. 4A). In the illustrated embodiment, the elongate member 200 is a hollow tube having a cylindrical wall 206 with a lumen 208 extending therein from a distal end 202 to a proximal end 204 of the tubular member 200. The tubular member 200 is composed of a suitable electrically conductive material, such as any of the materials described previously with reference to the electrodes 26.

Figure 4B:
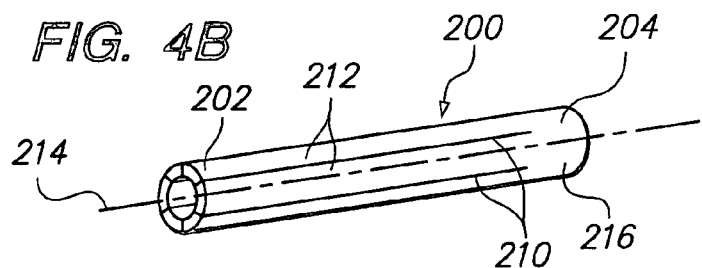

Next, a plurality of divisions 210 are formed through the wall 206 of the tubular member 200 using suitable means, such as laser cutting, mechanical cutting, chemical etching, etc. (FIG. 4B). The divisions 210 extend from the distal end 202 of the tubular member 200 towards the proximal end 204 of the tubular member 200 to form a plurality of tines 212. In the illustrated embodiment, the divisions 210 extend along the tubular member 200 parallel to the longitudinal axis 214 of the tubular member 200. The divisions 210 do not extend past the proximal end 204 of the tubular member 200, so that a common electrode base 216 for supporting the tines 212 is formed at the proximal end 204 of the tubular member 200. The distal tips of the tines 212 can be honed or sharpened, so that they are capable of penetrating tissue.

Figure 4C:
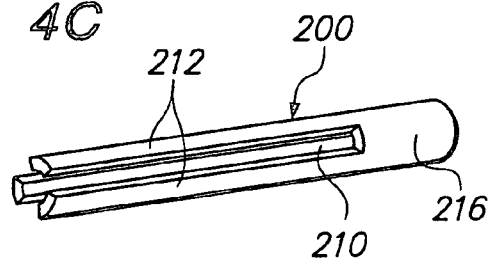

In the illustrated embodiment, six divisions 210 are formed in the wall 206, resulting in six tines 212. Alternatively, other numbers of tines can be formed from the tubular member 200 by forming a lesser or greater number of divisions 210 within the wall 206. In the embodiment illustrated in FIG. 4B, the divisions 210 are slits formed through the wall 206, resulting in tightly spaced tines 212 at the electrode base 216. Alternatively, the divisions 210 can take the form of slots having finite widths, resulting in loosely spaced tines 212 at the electrode base 216 (FIG. 4C). In this embodiment, three divisions 210 are formed in the wall 206, resulting in three tines 212.

Figure 4D:
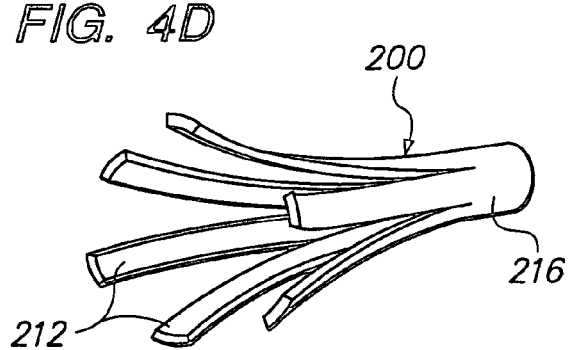

After the tines 212 have been formed, they are bent into proximally everted shapes (FIG. 4D). The tines 212 can then be heat treated, chemically treated, or processed by other methods, to set them in their bent configuration. It should be noted that the shape in which the tines 212 are bent is not limited to that shown in FIG. 4D, and thus, can have other shapes or configurations.

Figure 4E:
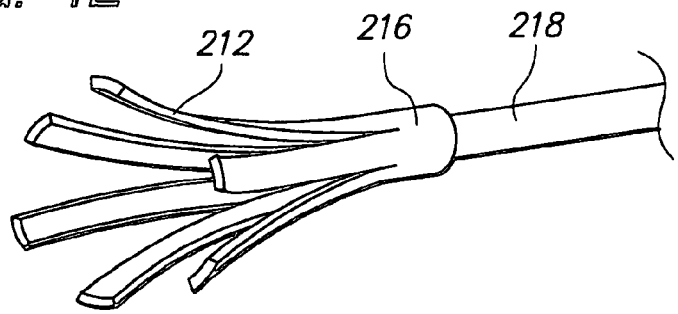

Next, the common electrode base 216 is secured to a distal end of a probe shaft 218 (FIG. 4E). The means used to secure the electrode base 216 to the probe shaft 218 will depend on the selected means for delivering RF energy to the tines 212. For example, if the body of the probe shaft 218 is used to deliver RF energy to the tines 212, in which case it will be composed of an electrically conductive material, the electrode base 216 can be secured to the probe shaft 218 by welding, soldering or brazing, such that electrode base 216 remains in electrical communication with the probe shaft 218. If separate RF wires are used to deliver RF energy to the tines 212, however, the electrode base 216 can be secured to the probe shaft by bonding with an electrically insulative agent.

As shown in the illustrated embodiment, constructing the tines 212 from the tubular member 200 obviates the need to attach the tines 212 to each other. Such technique also eliminates constructing each tine 212 individually, thereby reducing manufacturing time and improving manufacturing efficiency. Further, because such technique eliminates, or at least, reduces the total number of connections (e.g., welds, soldering) needed to secure the tines 212 to each other and/or to the shaft 218, the resulting probe assembly can have a substantially reduced cross sectional dimension. That is, the cross-sectional profile of the tines 212 at the electrode base 210 will be equal to or less than the cross-sectional profile of the electrode base 210, itself.

Before or after the electrode base 216, with the tines 212, are secured to the probe shaft 218, an RF connector (not shown) can be secured to the proximal end of the probe shaft 218 and placed into electrical communication with the tines 212 via the probe shaft 218 or separate RF wires (not shown) extending through the lumen of the probe shaft 218. The probe shaft 218 is then slidably mounted within a cannula (not shown) to form a probe assembly similar to the probe assembly 4 illustrated in FIGS. 1-3.

Figure 5A:
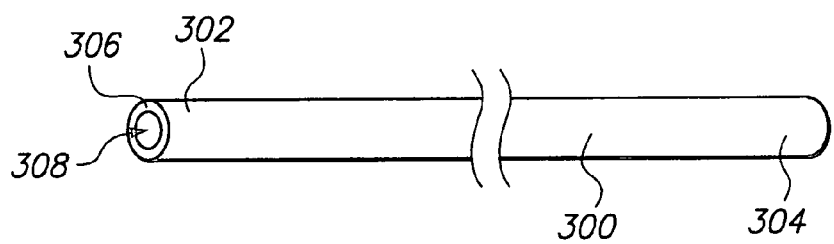

In the process illustrated in FIGS. 4A-4E, the electrode element (composed of the tines 212 and electrode base 216) and shaft 218 are discrete members that are formed and then subsequently secured to each other. In other processes, the electrode element and probe shaft can be formed as a unibody structure. For example, FIGS. 5A-5D illustrate one process for manufacturing a unibody electrode element and probe shaft. First, an elongate member 300 is provided (FIG. 5A). In the illustrated embodiment, the elongate member 300 is a hollow tube having a cylindrical wall 306 with a lumen 308 extending therein from a distal end 302 to a proximal end 304 of the tubular member 300. The tubular member 300 is composed of a suitable electrically conductive material, such as any of the materials described previously with reference to the electrodes 26. Notably, the elongate member 300 is significantly longer than the previous elongate member 200, since the elongate member 300 will also be used to form the probe shaft.

Figure 5B:
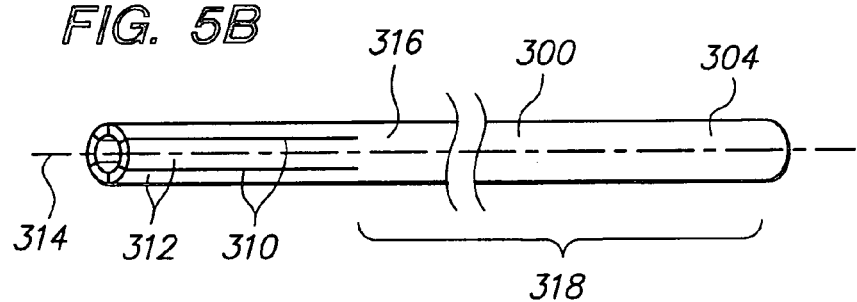

Next, a plurality of divisions 310 are formed through the wall 306 of the elongate member 300 using suitable means, such as laser cutting, mechanical cutting, chemical etching, etc. (FIG. 5B). The divisions 310 extend from the distal end 302 of the elongate member 300 towards the proximal end 304 of the elongate member 300 to form a plurality of tine 312. In the illustrated embodiment, the divisions 310 extend along the elongate member 300 parallel to a longitudinal axis 314 of the elongate member 300. The divisions 310 do not extend past the proximal end 304 of the elongate member 300, so that a relatively length probe shaft 318 remains, with the distal end of the probe shaft 316 forming an integrated common electrode base 316 for supporting the tine 312. The distal tips of the tine 312 can be honed or sharpened, so that they are capable of penetrating tissue.

Figure 5C:
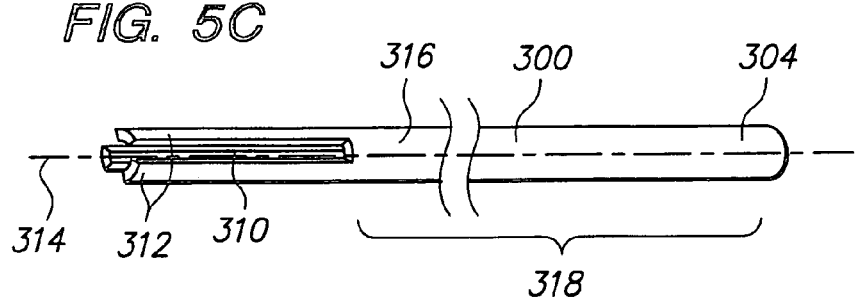

In the illustrated embodiment, six divisions 310 are formed in the wall 306, resulting in six tine 312. Alternatively, other numbers of tines can be formed from the tubular member 300 by forming a lesser or greater number of divisions 310 within the wall 306. In the embodiment illustrated in FIG. 5B, the divisions 310 are slits formed through the wall 306, resulting in tightly spaced tines 312 at the electrode base 316. Alternatively, the divisions 310 can take the form of slots having finite widths, resulting in loosely spaced tines 312 at the electrode base 316 (FIG. 5C). In this embodiment, three divisions 310 are formed in the wall 306, resulting in three tines 312.

After the tines 312 have been formed, they are bent into proximally everted shapes (FIG. 5D). The tines 312 can then be heat treated, chemically treated, or processed by other methods, to set them in their bent configuration. It should be noted that the shape in which the tines 312 are bent is not limited to that shown in FIG. 5D, and thus, can have other shapes or configurations. Unlike the previous embodiment, the tine 312 are already secured to the integrated electrode base formed at the distal end of the probe shaft 316. Thus, it can be appreciated that the process illustrated in FIGS. 5A-5D has the same advantages as the process illustrated in FIGS. 4A-4E, with the additional advantage of eliminating the need to separately secure the tine 312 to the shaft 318, thereby reducing manufacturing time and improving manufacturing efficiency, as well as further reducing the cross-sectional profile of the resulting assembly.

An RF connector (not shown) can be secured to the proximal end of the probe shaft 318 and placed into electrical communication with the tines 312 via the probe shaft 318 or separate RF wires (not shown) extending through the lumen of the shaft 318. The probe shaft 318 is then slidably mounted within a cannula (not shown) to form a probe assembly similar to the probe assembly 4 illustrated in FIGS. 1-3.

Figure 6D:
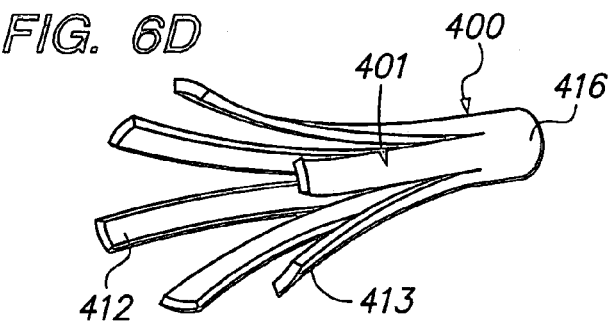

In the above-described processes, the electrode element (composed of the tines and electrode base) is formed of a unibody structure. In other processes, the electrode element can be formed of discrete structures that are subsequently integrated. For example, FIGS. 6A-6D illustrate one process for manufacturing and mounting a multi-member electrode element to a probe shaft. First, first and second elongate members 400 and 401 are provided (FIG. 6A). In the illustrated embodiment, the first elongate member 400 is a hollow tube having a cylindrical wall 406 with a lumen 408 extending therein from a distal end 402 to a proximal end 404 of the tubular member 400. The lumen 408 is size to allow the second tubular member 401 to be inserted therein. The second elongate member 401 is a hollow tube having a cylindrical wall 407 with a lumen 409 extending therein from a distal end 403 to a proximal end 405 of the tubular member 401. The tubular members 400, 401 are composed of a suitable electrically conductive material, such as any of the materials described previously with reference to the electrodes 26.

Next, divisions 410, 411 are formed through the respective walls 406, 407 of the tubular members 400, 401 using suitable means, such as laser cutting, mechanical cutting, chemical etching, etc. (FIG. 6B). The divisions 412, 413 extend from the respective distal ends 402, 403 of the tubular members 400, 401 towards the respective proximal ends 404, 405 of the tubular members 400, 401 to form respective pluralities of tines 412,413. In the illustrated embodiment, the divisions 410, 411 extend along the tubular members 400, 401 parallel to the longitudinal axes 414, 415 of the tubular members 400, 401. The divisions 412, 413 do not extend past the respective proximal ends 404, 405 of the tubular members 400, 401, so that common electrode bases 416, 417 for supporting the tines 412, 413 are formed. The distal tips of the tines 412, 413 can be honed or sharpened, so that they are capable of penetrating tissue. In the illustrated embodiment, three divisions 410 are formed in the wall 406 of the first tubular member 400, resulting in three tines 412. Likewise, three divisions 422 are formed in the wall 407 of the second tubular member 401, resulting in three tines 413. Alternatively, other numbers of tines can be formed from the tubular members 400, 401 by forming a lesser or greater number of divisions 410, 411 within the respective walls 406, 407. In this embodiment, the divisions 410, 411 take the form of slots having finite widths, resulting in loosely spaced tines 412, 413 at the respective electrode bases 416, 417.

Next, the second tubular member 401 is coaxially secured within the lumen 408 of the first tubular member 400 (FIG. 6C). In particular, the second tubular member 401 is oriented relative to the first tubular member 400, such that the slots 410 of the first tubular member 400 circumferentially align with the tines 413 of the second tubular member 401, and the slots 411 of the second tubular member 401 circumferentially align with the tines 412 of the first tubular member 400. In addition, the second tubular member 401 is preferably shorter than the second tubular member 400, so that after the two are secured together, the electrode base 417 of the second tubular member 401 is recessed distally within the electrode base 416 of the first tubular member 400, as shown in phantom in FIG. 6C. As will be described in further detail below, this reduces the cross-sectional mounting area of the assembly. The means used to secure the second tubular member 401 within the first tubular member 400 will depend on the desired electrically characteristics of the resulting electrode elements, and in particular, whether the resulting electrode elements will have monopolar or bipolar functionality. If the former, the tubular members 400, 401 will be electrically coupled to each other, in which case, the second tubular member 401 can be welded, soldered, or brazed within the first tubular member 400. If the latter, the tubular members 400, 401 will not be electrically coupled to each other, in which case, the second tubular member 401 is preferably bonded within the first tubular member 400 using a suitable electrically insulative bonding agent. Optionally, an electrically insulative layer (not shown) can be located between the tubular members 400, 401 to ensure that they are electrically isolated from each other.

After the tines 412, 413 have been formed, they are bent into proximally everted shapes (FIG. 6D). The tines 412, 413 can then be heat treated, chemically treated, or processed by other methods, to set them in their bent configuration. It should be noted that the shape in which the tines 420, 430 is bent is not limited to that shown in FIG. 6D.

Figure 6E:
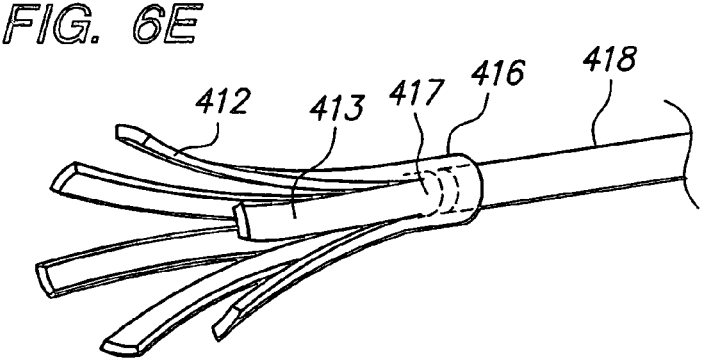

Next, the common electrode base 416 of the first tubular member 400 is secured to a distal end of a probe shaft 418 (FIG. 6E). This can be accomplished in the same manner as the previously described electrode base 216 of the tubular member 200 is secured to the probe shaft 218 illustrated in FIG. 4E. Alternatively, one of the tubular members 400, 401 can have a length that is longer than the other, such that a proximal portion of the tubular member with the longer length can be used as a probe shaft, as similarly discussed previously with reference to FIGS. 5A-5D.

Thus, it can be appreciated that the process illustrated in FIGS. 6A-6E has the same advantages as the process illustrated in FIGS. 4A-4E, with the additional advantage that bipolar functionality can be incorporated into the resulting assembly. It is noted that the mounting area on the probe shaft 418 is only increased by the wall thickness of the first tubular member 400, since the electrode base 417 of the second tubular member 401 is distally recessed within the electrode base 416 of the first tubular member 400, so that the distal edge of the probe shaft 418 abuts the proximal edge of the electrode base 416.

An RF connector (not shown) can be secured to the proximal end of the probe shaft 418 and placed into electrical communication with the tines 412, 413 via the probe shaft 418 or separate RF wires (not shown) extending through the lumen of the shaft 418. The probe shaft 418 is then slidably mounted within a cannula (not shown) to form a probe assembly similar to the probe assembly 4 illustrated in FIGS. 1-3.

It should be noted that the structure and geometry of the elongated members used to form the electrode elements and/or probe shafts are not limited to those described above, but can vary, depending on the desired application and results. For example, although the previously described elongated members are cylindrical in nature (i.e., they have circular cross-sectional profiles), an elongated member used to form electrode elements and/or probe shafts in accordance with the present invention can have other cross-sectional shapes, such as a elliptical, rectangular, triangular, pentagonal, octagonal, or other shapes.

Figure 7:
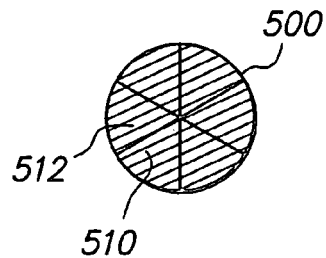
FIG. 7 illustrates a solid cross-section of an elongate member with divisions formed therein.

Also, although the use of hollow tubular members has the advantage of providing a convenient means for forming low-profile tines with generally rectangular geometries, tines can be formed from solid tubular members as well. For example, FIG. 7 illustrates the solid cross-section of an elongate member 500 with divisions 510 formed therein using suitable means, such as mechanical or laser cutting. As can be seen, each division 510 is formed through the entire diameter of the elongated member 500 to produce two tines 512 with pie-shaped cross-sections. Thus, in the illustrated embodiment, three divisions 510 are formed to produce a total of six tines 512. The tines 512 can then be subsequently shaped in the same manner that the previously described tines were shaped.

In addition, the geometrical characteristics of the divisions made through any given elongate member can be varied to select the different geometrical characteristics (e.g., shapes, profiles, orientations, and/or lengths) of the resulting tines.

Figure 8:
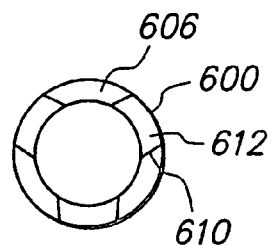
FIG. 8 is a cross sectional view of an elongate member with an alternative arrangement of electrode tines that can be constructed using methods illustrated in FIGS. 4A-4E and 5A-5D.

For example, although the divisions formed through the walls of the previously described tubular members extend through the centers of the respective tubular members, thereby creating tines with generally rectangular cross-sections, divisions can be tangentially formed through the tubular member. For example, FIG. 8 illustrates the cross-section of an elongate member 600, and in particular, a hollow tubular member, with divisions 610 formed through the wall 606 using suitable means, such as mechanical or laser cutting. As can be seen, each division 610 is a slit that is formed through the wall 606 of the tubular member 600 at a tangential angle, thereby creating tines 612 having generally trapezoidal cross-sections. Six divisions 610 are formed to create six tines 612.

Figure 9:
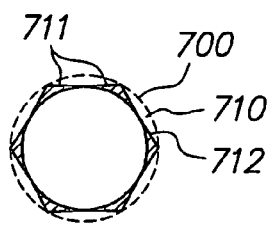
FIG. 9 is a cross sectional view of another elongate member with an alternative arrangement of electrode tines that can be constructed using methods illustrated in FIGS. 4A-4E, 5A-5D, and 6A-6E.

As another example, FIG. 9 illustrates the cross-section of another elongate member 700, and in particular, a hollow tubular member, with divisions 710 formed through the wall 706 using suitable means, such as mechanical or laser cutting. In this embodiment, each division is a slot formed by providing a pair of tangential cuts 711 that extend through the wall 706 towards each other. Six divisions 710 are formed to create six tines 712 with generally triangular cross-sections.

Figure 10:
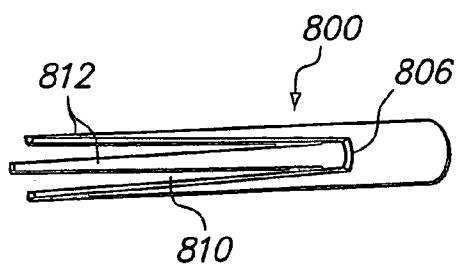
FIG. 10 is a cross sectional view of still another elongate member with an alternative arrangement of electrode tines that can be constructed using methods illustrated in FIGS. 4A-4E, 5A-5D, and 6A-6E.

Although the slots formed through the walls of the previously described tubular members were rectangular in nature, thereby resulting in tines with substantially uniform widths along their lengths, the slots can have other shapes. For example, FIG. 10 illustrates an elongate member 800, and in particular, a hollow tubular member, with divisions 810 in the form of tapered slots that are formed through the wall 806 using suitable means, such as laser cutting, mechanical cutting, chemical etching, etc. As a result, triangular-shaped tines 812 that taper to a distal point are created.

Although the tines have been previously described to have the same geometrical characteristics for any given embodiment, the geometrical characteristics of the tines may differ within the same embodiment. For example, for a given embodiment, some of the divisions may be slits and other divisions may be slots. Or some of the slots may have a uniform width, and others may have a non-uniform width. Or some of the divisions may be longer than others to vary the lengths of the tines within the same embodiment.

Figure 11A:
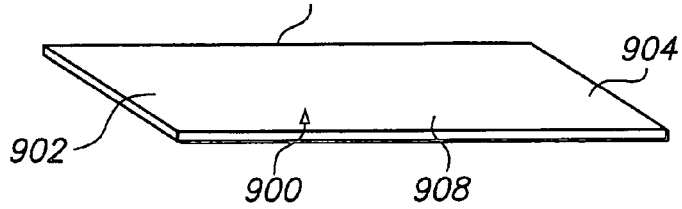
FIGS. 11A-11E are perspective views illustrating yet another method of constructing the ablation probe of FIGS. 2 and 3.

Although the previously described processes utilized a preformed elongate member on which the divisions were formed, the divisions can be formed into a material that is then subsequently formed into an elongate member. FIGS. 11A-11D illustrates an example of such a process. First, a rectangular, flat, sheet 900 having first and second opposing edges 902, 904 and third and fourth opposing edges 906, 908 is provided (FIG. 11A). The sheet 900 is composed of a suitable electrically conductive material, such as any of the materials described previously with reference to the electrodes 26.

Figure 11B:
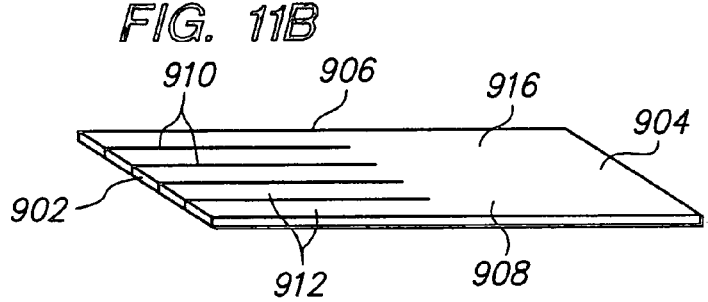
Figure 11C:
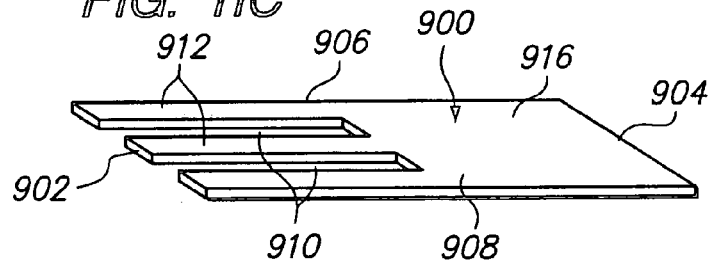

Next, a plurality of divisions 910 are formed through the wall sheet 900 using suitable means, such as laser cutting, mechanical cutting, chemical etching, etc. (FIG. 11B). The divisions 910 extend from the first end 902 of the sheet 900 towards the second opposing end 904 of the sheet 900 to form a plurality of tines 912. The divisions 910 do not extend past the second end 904, so that a common electrode base 916 for supporting the tines 912 is formed at the second end 904 of the sheet 900. The distal tips of the tines 912 can be honed or sharpened, so that they are capable of penetrating tissue. In the illustrated embodiment, five divisions 910 are formed in the sheet 900, resulting in six tines 912. Alternatively, other numbers of tines can be formed from the sheet 900 by forming a lesser or greater number of divisions 910 therein. In the embodiment illustrated in FIG. 11B, the divisions 910 are slits formed through the sheet 900, resulting in tightly spaced tines 912 at the electrode base 916. Alternatively, the divisions 910 can take the form of slots having finite widths, resulting in loosely spaced tines 912 at the electrode base 916 (FIG. 11C). In this embodiment, two divisions 910 are formed in the sheet 900, resulting in three tines 912.

In the illustrated embodiment, the divisions 910 extend along the sheet 900 parallel to opposing third and fourth ends 906, 908, which result in rectangular tines. Alternatively, the divisions 910 may have other shapes, profiles, orientations, and/or lengths to form tines have other geometries. In the illustrated embodiment, the divisions 910 are made in a direction (or orientation) that is approximately perpendicular to a surface of the sheet 900. Alternatively, the divisions 910 can be made at other directions (or orientations) to form desired cross sectional shapes for the tines 912. In addition, instead of forming the tines with the same geometries, the tines may be formed with different geometries in the same embodiment.

Figure 11D:
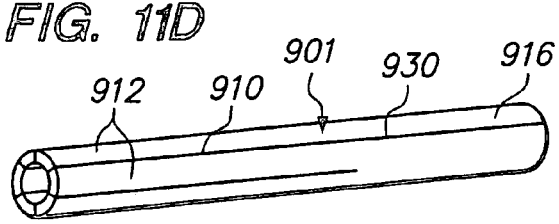

Next, the third and fourth opposing ends 906, 908 of the sheet 900 are rolled or bent towards each other to form an elongate member 901, and in particular, a hollow tubular member (FIG. 11D). The third and fourth opposing ends 906, 908 can be abutted to form a seam 930, and the affixed to each other using suitable means, such as welding, soldering, brazing, etc., to prevent the tubular member 901 from unwinding itself. In the illustrated embodiment, the tubular member 901 has an exterior cross sectional profile that is circular. Alternatively, the tubular member 901 can have other cross sectional shapes, such as an elliptical, rectangular, triangular, pentagonal, octagonal, or other shapes. In an alternative process, instead of rolling or bending the sheet 900 to form the tubular member 901 after the tines 912 are made, the sheet 900 can be rolled or bent into the elongate member 901 before the tines 912 are made. In other processes, instead of forming the tines 912 using a single sheet, a plurality of sheets can be used to form the tines 912. In such cases, after the sheets are rolled or bent into respective elongate members, the elongate members can be placed coaxially relative to each other, as similarly discussed previously with reference to FIG. 6C.

Figure 11E:
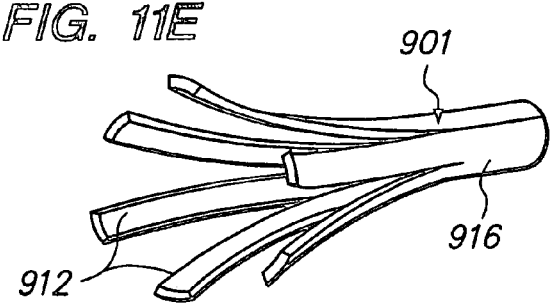

After the tines 912 have been formed, they are bent into proximally everted shapes (FIG. 11E). The tines 912 can then be heat treated, chemically treated, or processed by other methods, to set them in their bent configuration. It should be noted that the shape in which the tines 912 are bent is not limited to that shown in FIG. 11E, and thus, can have other shapes or configurations. In other processes, instead of shaping the tines 912 after the sheet 900 is rolled or bent into the elongate member 901, the tines 912 can be shaped prior to rolling or bending the sheet 900 into the tubular member 901.

Next, the common electrode base 916 is secured to a distal end of a probe shaft, the RF connector is secured to the proximal end of the probe shaft, and the probe shaft is slidably mounted in a cannula in the same manner previously described with respect to FIG. 4E. In an alternative process, the sheet 900 can have a relatively longer length, such that when the sheet 900 is rolled or bent into the elongate member 901, the proximal portion of the elongate member 901 can be used as the probe shaft, as similarly discussed previously with reference to FIGS. 5A-5D.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated. Thus, the present invention is intended to cover alternatives, modifications, and equivalents that may fall within the spirit and scope of the present invention as defined by the claims.

What is claimed:

1. A tissue ablation probe, comprising:
   a probe shaft having a proximal and a distal end; and
   a unibody electrode element comprising a common electrode base located at the distal shaft end and a plurality of electrode tines distally extending from the electrode base; and
   another unibody electrode element comprising another common electrode base axially secured to the electrode base and another plurality of electrode tines distally extending from the other electrode base, wherein the other electrode base is coaxially secured within a lumen of the electrode base, and the other tines of the other electrode element are circumferentially staggered between the respective tines of the electrode element.

2. The probe of claim 1, wherein the electrode element and shaft are formed as a unibody structure.

3. The probe of claim 1, wherein the electrode element and shaft are formed as discrete members.

4. The probe of claim 1, wherein the probe shaft is rigid.

5. The probe of claim 1, wherein the electrode base and probe shaft are cylindrical.

6. The probe of claim 1, wherein the electrode tines are tightly spaced at the electrode base.

7. The probe of claim 1, wherein the electrode tines are loosely spaced at the electrode base.

8. The probe of claim 1, wherein the electrode element is electrically coupled to the probe shaft.

9. The probe of claim 1, further comprising a radio frequency connector secured to the proximal shaft end and electrically coupled to the electrode element.

10. The probe of claim 1, further comprising a cannula, wherein the probe shaft is slidably disposed within the cannula so that the electrode element can be alternately placed in a deployed configuration and a retracted configuration.

11. The probe of claim 1, wherein the electrode tines are pre-shaped to form a proximally everted shape.

12. The probe of claim 1, wherein the tines are composed of a resilient material.

13. The probe of claim 1, wherein the tines have tissue-penetrating distal tips.

14. The probe of claim 1, wherein the electrode tines have distal ends that are separated from each other.

15. The probe of claim 1, wherein the other electrode tines have other distal ends that are separated from each other.

16. A tissue ablation probe, comprising:
   an elongate probe shaft having a proximal and a distal end;
   a common electrode base located at the distal shaft end, the electrode base having a first cross-sectional profile;
   an array of electrode tines distally extending from the electrode base, the electrode array having a second cross-sectional profile at the electrode base that is equal to or less than the first cross-sectional profile;
   another common electrode base coaxially arranged with the electrode base, the other electrode base having a third cross-sectional profile, wherein the other electrode base is coaxially secured within a lumen of the electrode base; and
   another array of electrode tines distally extending from the other electrode base, the electrode array having a fourth cross-sectional profile at the electrode base that is equal to or less than the third cross-sectional profile, wherein the other tines of the other electrode base are circumferentially staggered between the respective tines of the electrode base.

17. The probe of claim 16 wherein the first and second cross-sectional profiles are equal.

18. The probe of claim 16, wherein the electrode base is electrically conductive.

19. The probe of claim 16, wherein the electrode array and electrode base are formed as discrete members.

20. The probe of claim 16, wherein the electrode base and probe shaft are formed as a unibody structure.

21. The probe of claim 16, wherein the electrode base and probe shaft are formed as discrete members.

22. The probe of claim 16, wherein the probe shaft is rigid.

23. The probe of claim 16, wherein the electrode base and probe shaft are cylindrical.

24. The probe of claim 16, wherein the electrode tines are tightly spaced at the electrode base.

25. The probe of claim 16, wherein the electrode tines are loosely spaced at the electrode base.

26. The probe of claim 16, wherein the electrode base is electrically coupled to the probe shaft.

27. The probe of claim 16, further comprising a radio frequency connector secured to the proximal shaft end and electrically coupled to the electrode array.

28. The probe of claim 16, further comprising a cannula, wherein the probe shaft is slidably disposed within the cannula so that the array of electrode tines distally extending from the electrode base can be alternately placed in a deployed configuration and a retracted configuration.

29. The probe of claim 16, wherein the electrode tines are pre-shaped to form a proximally everted shape.

30. The probe of claim 16, wherein the tines are composed of a resilient material.

31. The probe of claim 16, wherein the tines have tissue-penetrating distal tips.

32. The probe of claim 16, wherein the electrode tines have distal ends that are separated from each other.

33. The probe of claim 16, wherein the other electrode tines have other distal ends that are separated from each other.

* * * * *